(12) United States Patent
Grill

(10) Patent No.: US 9,005,337 B2
(45) Date of Patent: Apr. 14, 2015

(54) SYSTEM FOR THE TREATMENT AND PURIFICATION OF BIOGAS

(75) Inventor: Jeffrey J. Grill, Long Beach, CA (US)

(73) Assignee: Clean Energy Renewable Fuels, LLC, Newport Beach, CA (US)

( * ) Notice: Subject to any disclaimer, the term of this patent is extended or adjusted under 35 U.S.C. 154(b) by 377 days.

(21) Appl. No.: 13/557,004

(22) Filed: Jul. 24, 2012

(65) Prior Publication Data

US 2013/0095014 A1    Apr. 18, 2013

Related U.S. Application Data

(63) Continuation-in-part of application No. 13/276,199, filed on Oct. 18, 2011, now Pat. No. 8,535,429, and a continuation-in-part of application No. 13/276,205, filed on Oct. 18, 2011, now Pat. No. 8,574,888, and a continuation-in-part of application No. 13/276,207, filed on Oct. 18, 2011.

(51) Int. Cl.
*B01D 53/22* (2006.01)
*B01D 53/75* (2006.01)
*C12M 1/00* (2006.01)

(52) U.S. Cl.
CPC .......... *B01D 53/75* (2013.01); *B01D 2257/304* (2013.01); *B01D 2257/504* (2013.01); *B01D 2258/05* (2013.01); *C12M 47/18* (2013.01)

(58) Field of Classification Search
None
See application file for complete search history.

(56) References Cited

U.S. PATENT DOCUMENTS

| 5,352,115 A | 10/1994 | Klobucar |
| 8,480,789 B2 * | 7/2013 | Sorensen et al. ................. 95/50 |
| 2005/0132883 A1 | 6/2005 | Su et al. |
| 2007/0095205 A1 * | 5/2007 | Palumbo ........................ 95/51 |
| 2009/0029062 A1 | 1/2009 | Bar |
| 2010/0063343 A1 * | 3/2010 | Cusumano et al. .......... 585/800 |
| 2010/0275781 A1 | 11/2010 | Tsangaris et al. |

(Continued)

FOREIGN PATENT DOCUMENTS

| GB | 2207872 | 2/1989 |
| WO | 99/29413 | 6/1999 |

OTHER PUBLICATIONS

Patent Cooperation Treaty, International Search Report, PCT/US2012/060882, Dec. 17, 2012, pp. 1-2.

(Continued)

*Primary Examiner* — Duane Smith
*Assistant Examiner* — Pankti Patel
(74) *Attorney, Agent, or Firm* — Sheppard Mullin Richter & Hampton LLP

(57) ABSTRACT

A system and method for the purification of biogas, the system comprising: a gas compressor for increasing the pressure of the biogas for processing; a gas processor for removing any $CO_2$, volatile organic compounds, and $H_2S$, from the gas; an optional biological sulfur removal system for treating offgas from the gas processor; a regenerative thermal oxidizer system for treating gas from the biological sulfur removal system for thermal destruction of volatile organic compounds, $H_2S$, and $CH_4$ slipped from the gas processor; a catalytic oxygen removal system for receiving product gas from the gas processor and removing oxygen from the product gas; and a caustic scrubber for receiving product gas from the catalytic oxygen removal system and neutralizing any acid formed during catalytic oxygen removal.

12 Claims, 5 Drawing Sheets

(56) References Cited

U.S. PATENT DOCUMENTS

2010/0292524 A1* 11/2010 Turner et al. .................. 585/802
2011/0091953 A1    4/2011 Bolin et al.
2012/0264197 A1* 10/2012 Mitariten ...................... 435/266
2013/0205828 A1*  8/2013 Sethna et al. ................... 62/607

OTHER PUBLICATIONS

Patent Cooperation Treaty, International Search Report, PCT/US2012/060886, Jan. 7, 2013, pp. 1-2.

* cited by examiner

SYSTEM FOR THE TREATMENT AND PURIFICATION OF BIOGAS

REFERENCE TO RELATED APPLICATIONS

This application is a continuation-in-part of U.S. patent application Ser. Nos. 13/276,205, 13/276,199 and 13/276,207, each filed on Oct. 18, 2011, the contents of which are incorporated herein by reference in their entireties.

FIELD OF THE INVENTION

The invention broadly relates to systems for the treatment and purification of biogas.

BACKGROUND OF THE INVENTION

Biogas refers to a gaseous fuel produced by the biological breakdown of organic matter in the absence of oxygen. It is produced by the anaerobic digestion or fermentation of biodegradable materials such as biomass, manure, sewage, municipal waste, green waste, plant material and crops. Biogas primarily comprises methane and carbon dioxide, and may contain small amounts of hydrogen sulfide, moisture and siloxanes.

The gases methane, hydrogen, carbon monoxide, and any other hydrocarbon (e.g., ethane, propane, butane, etc.) can be combusted or oxidized with oxygen. This energy release allows biogas to be used as a fuel. Biogas can be used as a fuel for any heating purpose. It can also be produced by anaerobic digesters where it is typically used in a gas engine to convert the chemical energy of the gas into electricity and heat. Anaerobic digestion is a series of processes in which microorganisms break down biodegradable material in the absence of oxygen, also used for industrial or domestic purposes to manage waste and/or to release energy.

The digestion process begins with bacterial hydrolysis of the input materials in order to break down insoluble organic polymers such as carbohydrates and make them available for other bacteria. Acidogenic bacteria then convert the sugars and amino acids into carbon dioxide, hydrogen, ammonia, and organic acids. These bacteria then convert these resulting organic acids into acetic acid, along with additional ammonia, hydrogen, and carbon dioxide. Finally, methanogens convert these products to methane and carbon dioxide.

Anaerobic digesters can use a multitude of feed stocks for the production of methane rich bio-gas including but not limited to purpose-grown energy crops such as maize. Landfills also produce methane rich bio-gas through the anaerobic digestion process. As part of an integrated waste management system, this bio-gas may be collected and processed for beneficial use while simultaneously reducing greenhouse gas emissions into the atmosphere.

Anaerobic digestion is widely used as a source of renewable energy. The process produces a biogas that can be used directly as cooking fuel, in combined heat and power gas engines or upgraded to natural gas quality biomethane. The utilization of biogas as a fuel helps to replace fossil fuels. The nutrient-rich digestate and/or Leachate that is also produced can be used as fertilizer.

$H_2S$ is a common contaminant in biogas applications such as landfills and digesters. Previously, biological $H_2S$ systems have been used for the removal of $H_2S$ from such biogas applications. In some cases, biological $H_2S$ removal systems can be several orders in magnitude lower in cost than expensive sulfur removal systems such as media or iron chelating systems. However, conventional biological systems can require more than 2% oxygen to maintain a stable removal rate of $H_2S$, and most raw gas from landfills and digesters contains far less than 2% oxygen. Accordingly, the raw gas from landfills and digesters cannot be processed using a conventional biological $H_2S$ removal system due to the scarcity of oxygen.

In biogas applications such as landfills and digesters, $H_2S$ and other impurities including halides and halogenated compounds are frequently present in low percent to ppm/ppb quantities. These compounds may dissociate at high temperatures and in the presence of water to form caustic acids including, but not limited to $H_2S$, HF, $H_2SO_4$, $H_3PO_4$ and $HNO_3$. Typical metallurgy such as carbon and stainless steels are susceptible to corrosion and failure when placed into contact with these acids. Downstream equipment that changes the dew point and allows condensation to occur may concentrate these acids in pooling areas such as moisture separators, chillers, and gas coolers.

Gas processing techniques and other unit operations may produce acids form gas constituents. However, these systems merely employ acid neutralization after the acids have formed and concentrated in the pooling areas. As such, these conventional systems simply act as a band aid to condensation. Caustic scrubbers have been used in the past for several applications. For example, they may be used for $CO_2$ removal, $H_2S$ removal and also for the removal of several other reactive contaminants in both liquid and gaseous phase.

The technical expertise required to maintain industrial scale anaerobic digesters coupled with high capital costs and low process efficiencies have limited the level of its industrial application as a waste treatment technology. As a result, it is imperative that anaerobic digesters and biogas treatment plants operate at the highest possible efficiency.

SUMMARY OF THE INVENTION

An embodiment of the present invention is directed toward a system for the purification of biogas, comprising: a gas compressor for increasing the pressure of the biogas for processing; a gas processor for removing any $CO_2$, volatile organic compounds, and $H_2S$, from the gas; a biological sulfur removal system for treating offgas from the gas processor; a regenerative thermal oxidizer system for treating gas from the biological sulfur removal system for thermal destruction of volatile organic compounds, $H_2S$, and $CH_4$ slipped from the gas processor, thereby concentrating and purifying the $CH_4$; a catalytic oxygen removal system for receiving product gas from the gas processor and removing oxygen from the product gas; and a caustic scrubber for receiving product gas from the catalytic oxygen removal system and neutralizing any acid formed during catalytic oxygen removal.

In the above-described system for the purification of biogas, the biological sulfur removal system may comprise a housing that receives gas from the gas processor through a gas inlet, and the housing can comprise a plurality of layers through which the gas flows while it is treated for $H_2S$ removal, and a gas outlet through which treated gas exits. In one embodiment, a first layer comprises a lower layer including a first mixing media, and a second layer comprising a second mixing media is disposed above the first layer and. A third layer is disposed above the second layer comprising at least one sprayer of a solution for $H_2S$ removal, wherein the at least one sprayer is used to spray a neutralizing agent, hydrating agent, or nutrients on the gas as it flows through the housing. Neutralization typically occurs in a tank that collects the condensate from the $H_2S$ removal system. The neutralizing agent is selected from the group consisting of: water solutions, caustic solutions, and basic solutions such as NaOH solutions of varying pH for $H_2S$ removal. In some cases, a fourth layer comprising a top layer of activated carbon is disposed above the third layer.

The regenerative thermal oxidizer system may comprise: a recuperative heat exchanger that receives gas from the biological sulfur removal system or gas processor and boosts an inlet gas temperature of the gas to a second gas temperature; and a regenerative thermal oxidizer that receives the gas from the heat exchanger, further heats the gas to a third exhaust temperature, and feeds the gas back through the recuperative heat exchanger, which recoups heat from the gas such that the exhaust exits the heat exchanger at a fourth gas temperature. In addition, the caustic scrubber may comprise a vertical column having a top and a bottom and including a counter current flow system, wherein the process gas flows up vertically through the column in counter current flow to a caustic liquid solution that flows downward through the column. In some embodiments, the caustic liquid solution removes at least one acid from the process gas such that treated gas that is substantially free of acids bubbles out through an opening at the top of the vertical column. The at least one acid can be selected from the group consisting of $H_2S$, HF, $H_2SO_4$, $H_3PO_4$ and $HNO_3$. The caustic liquid solution may comprise an NaOH solution.

System for Treating Offgas

Another embodiments of the present invention is directed toward a method for the purification of biogas, comprising: increasing the pressure of the biogas using a gas compressor; removing any $CO_2$, volatile organic compounds, and $H_2S$, from the gas using a gas processor; optionally treating offgas (including any $H_2S$) from the gas processor using an optional biological sulfur removal system; treating gas from the biological sulfur removal system using a regenerative thermal oxidizer system; receiving product gas from the gas processor and removing oxygen from the product gas using a catalytic oxygen removal system; and receiving product gas from the catalytic oxygen removal system and neutralizing any acid formed during catalytic oxygen removal using a caustic scrubber.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Biogas is a renewable energy composed primarily of methane resulting from the natural decomposition of organic waste by anaerobic bacteria. Similar to natural gas, methane captured by a biogas system can be used to provide heat, electrical power or transportation biofuel. Biogas extraction can be used to: (i) produce green and renewable energy; (ii) reduce pollution and greenhouse gases; (iii) reduce waste odors and pathogens; and transform waste into valuable bio-fertilizer.

Fermentation, or anaerobic digestion, is the most common process that breaks down the organic waste. The organic waste may then be oxidized, thereby creating energy. Various types of organic materials include, but are not limited to: (i) biomass, (ii) landfill waste, (iii) sewage, (iv) manure, and (v) plant material. The most common gases produced are methane and carbon dioxide. Other gases that can be formed include hydrogen, nitrogen, and carbon monoxide. Methane, hydrogen, carbon monoxide and any other hydrocarbon (e.g., ethane, propane, butane, etc.) can be combusted to create heat and electricity. When biogas is created from existing waste streams, it reduces odors and methane emissions and creates two renewable resources. Methane is a potent greenhouse gas that contributes to global climate change. It is expected that a landfill gas energy project will capture about 30% to 99% of the methane emitted from the landfill, depending on system design and effectiveness.

There are two primary methods of recovering biogas for use as energy, namely: (i) by creating an anaerobic digestion system to process waste, most commonly manure or other wet biomass, and (ii) by recovering natural biogas production formed in existing landfills. Once recovered, biogas can be converted to energy using a number of methods.

Figure 1:
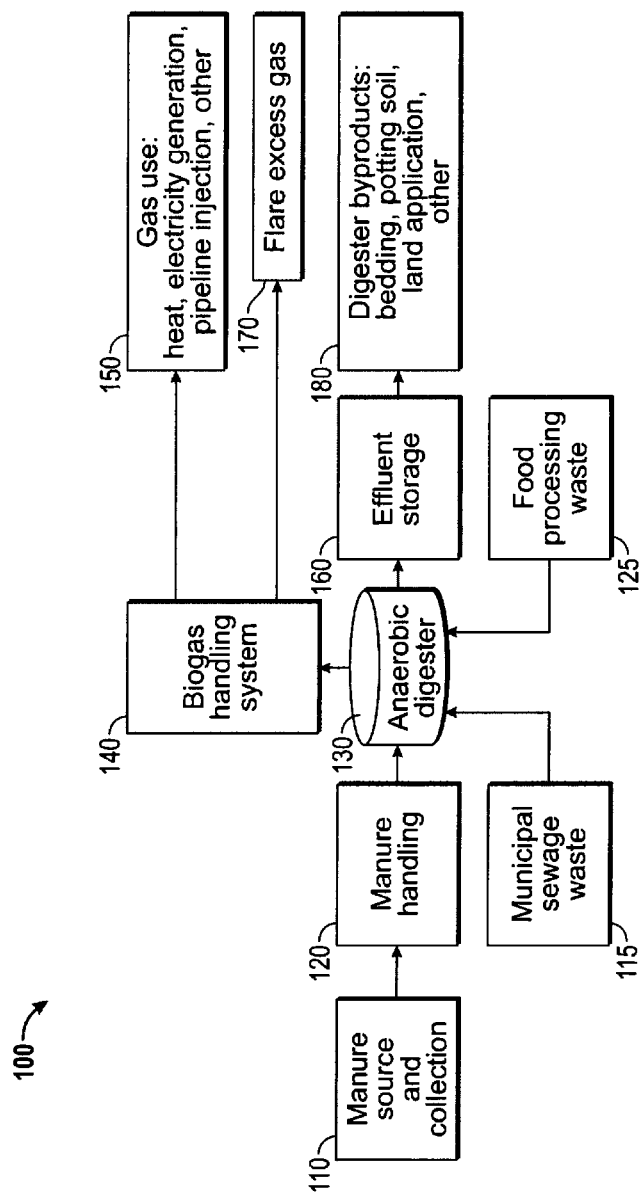
FIG. 1 is a flow diagram illustrating the stages of an exemplary anaerobic digestion system.

FIG. 1 is a flow diagram illustrating the stages of an exemplary anaerobic digestion system 100. Specifically, the an anaerobic digestion system 100 comprises a manure collection system 110, a manure handling system 120, a municipal sewage waste system 115, a food processing waste system 125, an anaerobic digester 130, a biogas handling system 140, gas use devices 150, an effluent storage 160. In addition, at least one flare 170 may be used to burn excess gas. Digester products 180 may be used for bedding, potting soil, land applications, etc. More particularly, manure collection system 110 is used to gather manure and transport it to the anaerobic digester 130. In some cases, existing liquid/slurry manure management systems can be adapted to deliver manure to the anaerobic digester 130. The anaerobic digester 130 may be designed to stabilize manure and optimize the production of methane. A storage facility for digester effluent, or waste matter, may also be required. In some embodiments, waste from a municipal sewage waste system 115 and/or a food processing waste system 125 is transported and fed into to the anaerobic digester 130.

With further reference to FIG. 1, the anaerobic digester 130 outputs biogas into the biogas handling system 140. The biogas may contain approximately 60% methane and 40% carbon dioxide. It is collected, treated, and piped to a gas use device 150. By way of example, the biogas can then be upgraded to natural gas pipeline quality. It may also be used to generate electricity, as a boiler fuel for space or water heating, or for a variety of other uses. At least one flare 170 is also installed to destroy extra gas and as a back-up mechanism for the primary gas use device 160.

The anaerobic digester 130 may be made out of concrete, steel, brick, or plastic. Additionally, the digester 130 includes a tank for pre-mixing the waste and a digester vessel. In some embodiments, the anaerobic digester 130 may comprise a batch digesters or a continuous digester. A batch digester is loaded with organic materials, which are allowed to digest therein. The retention time depends on temperature and other factors. Once the digestion is complete, the effluent is removed and the process is repeated.

In further embodiments, the anaerobic digester 130 may comprise a continuous digester, wherein organic material is constantly or regularly fed into the digester, and wherein the material moves through the digester either mechanically or by the force of the new feed. Unlike batch-type digesters, continuous digesters produce biogas without the interruption of loading material and unloading effluent. Various types of continuous digesters include vertical tank systems, horizontal tank or plug-flow systems, and multiple tank systems.

Anaerobic digestion also occurs naturally underground in landfills, wherein the waste is covered and compressed by the weight of the material that is deposited above. This material prevents oxygen exposure, thereby allowing chemical reactions and microbes to act upon the waste. This encourages an uncontrolled process of biomass decay. The rate of production is affected by waste composition and landfill geometry. Landfill gas may comprise about 40% to 60% methane, and about 40% to 60% carbon dioxide.

Figure 2:
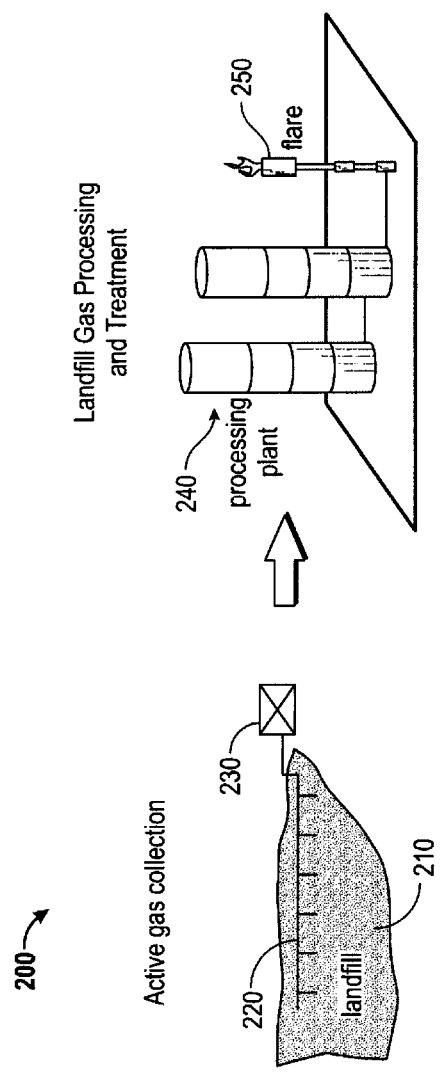
FIG. 2 is a diagram illustrating the stages of an exemplary landfill gas system.

FIG. 2 is a diagram illustrating an exemplary landfill gas system 200 including landfill 210, landfill gas wells 220 for active gas collection, landfill gas wellhead 230, landfill gas processing and treatment plant 240, and at least one landfill gas flare 250. Landfill gas is extracted from landfill 210 using a series of wells 220 and a blower/flare system. The landfill gas system 200 directs the collected gas to landfill gas processing and treatment plant 240, where it is processed and treated.

$H_2S$ is a common contaminant in biogas applications such as landfills and digesters. Previously, biological $H_2S$ systems have been used for the removal of $H_2S$ from such biogas applications. In some cases, biological $H_2S$ removal systems can be several orders in magnitude lower in cost than expensive sulfur removal systems such as media or iron chelating systems. However, conventional biological systems can require more than 2% oxygen to maintain a stable removal rate of $H_2S$, and most raw gas from landfills and digesters contains far less than 2% oxygen. For example, the oxygen level in a typical raw feed can be around 0.5% oxygen. Accordingly, the raw gas from landfills and digesters cannot be processed using a conventional biological $H_2S$ removal system due to the scarcity of oxygen.

Figure 3:
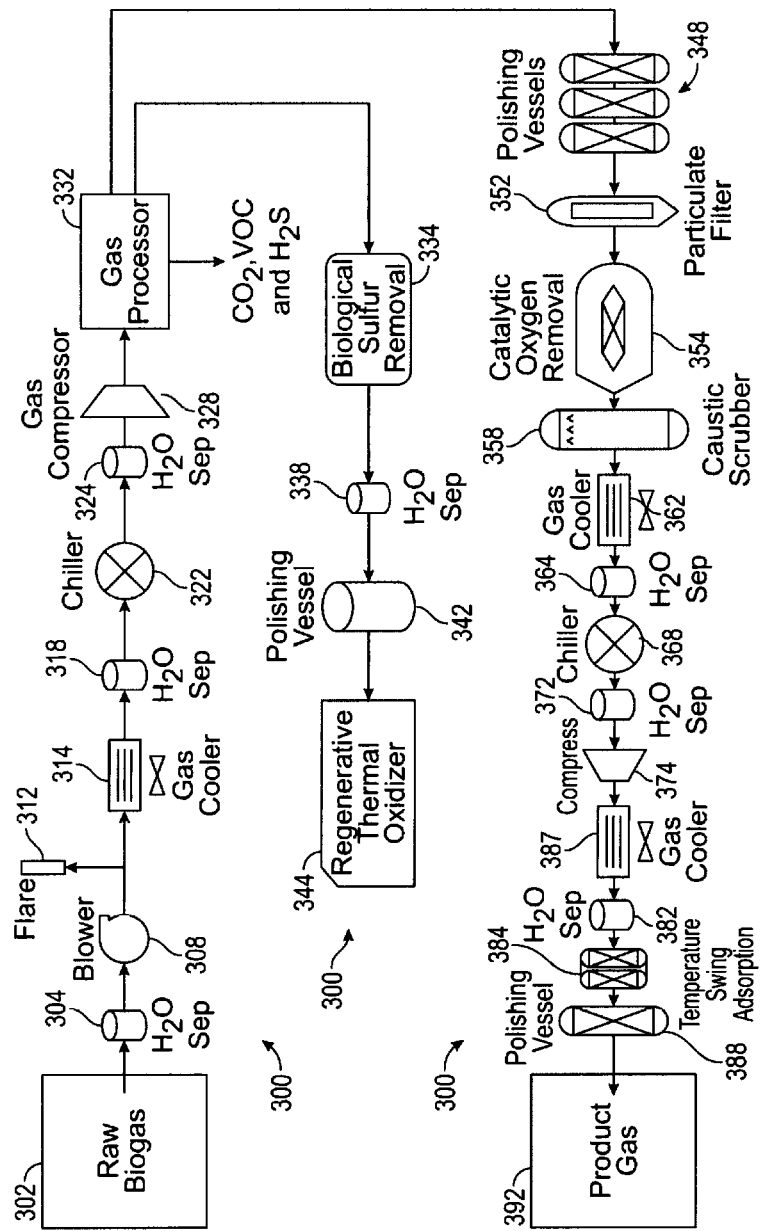
FIG. 3 is a flow diagram illustrating a system and method for the purification of biogas, in accordance with an embodiment of the invention.

FIG. 3 is a flow diagram illustrating a system and method 300 for the treatment of biogas, in accordance with an embodiment of the invention. In particular, raw biogas 302 is assumed to be dirty and wet, e.g., when extracted from a landfill or received from a digester. In the illustrated embodiment, the raw biogas 302 is approximately 100° F. and approximately −2 PSIG. Once collected, it passes through a moisture separator 304 comprising a vessel with internal baffling or pads that remove an appropriate and desired amount of moisture from this saturated gas stream. The gas stream then passes through a vacuum blower 308 or compressor which creates suction on the landfill and generates a positive gas pressure for the downstream equipment. This blower 308 can be either centrifugal, positive displacement, or any other configuration that allows for the generation of a positive pressure at the system's discharge. Compression both facilitates drying (dew point change) and drives the flow of gas through the plant.

With further reference to FIG. 3, the gas can be destroyed by a flare 312, sent to an engine for electricity generation, or sent to a gas processing plant, whereby a gas cooler 314 is employed to reduce the gas temperature from the gain of heat through compression. The gas cooler 314 may comprise a tube bank heat exchanger with one or more forced draft fans to cool the gas with ambient air. A moisture separator 318 is then used to remove liquid droplets and condensate from the gas phase. A gas chiller 322 is used to reduce the gas dewpoint, thereby further removing excess water and particulates. This moisture is removed by another moisture separator 324. The gas is then passed though a gas compressor 328 to increase the pressure of the gas for processing. By way of example, the gas compressor 328 may comprise a positive displacement, flooded screw, sliding vane, or any other type of gas compressor for compressing the gas to the desired level. The gas is then passed though a gas processor 332, which removes $CO_2$, volatile organic compounds (VOCs), and $H_2S$, thereby concentrating and purifying the $CH_4$. Gas processor 332 may comprise membranes, pressure swing adsorbers, solvents, or a cryogenic means of separation. In some embodiments, the gas compressor 328 is a component of the gas processor 332. In some configurations, an optional nitrogen removal component is provided either between gas compressor 328 and gas processor 332, or between gas processor 332 and polishing vessels 348. Alternatively, the optional nitrogen removal component may be located at any point in the system 300 after the gas compressor 328.

The offgas (including the VOCs and $H_2S$) produced by gas processor 332 is optionally sent to an optional biological sulfur removal system 334. This system may comprise a biological system featuring a solid or liquid sorption process. One embodiment of the biological sulfur removal system 334 is described hereinbelow with respect to FIG. 4. The gas then passes through another moisture separator 338 to remove excess water, and is then sent to a polishing vessel 342 to remove any unwanted constituents, including, but not limited to: sulfuric acid, siloxanes and $H_2S$. The gas is then optionally passed to an optional regenerative thermal oxidizer 344, or to an engine for electricity. One embodiment of the regenerative thermal oxidizer 344 is described hereinbelow with respect to FIG. 5.

With continued reference to FIG. 3, the product gas from the gas processor 332 is sent though a gas polishing system including at least one polishing vessel 348, which may comprise solid or liquid media to remove unwanted gas constituents. Such media may include without limitation: activated carbon, silica gel, zeolite, and/or alumina. The gas is then sent to a particulate filter 352 comprising at least one filter element that can be designed to achieve the appropriate level of micron or sub-micron particle filtration. The gas is then passed through a catalytic oxygen removal system 354 that may comprise a recuperative gas heat exchanger, a gas heater, and a catalyst. Since small levels of acids may be formed during catalytic oxygen removal, a caustic scrubber 358 is used for neutralization. By way of example, the caustic scrubber 358 may comprise a vessel with gas flowing in an upward vertical motion in counter flow with a caustic liquid to strip the gas of acids. The removal of acids may additionally be accomplished with a caustic impregnated solid media. One embodiment of the caustic scrubber 358 is described hereinbelow with respect to FIG. 6. The combination of the polishing vessel 348, particulate filter 352, catalytic oxygen removal system 354 and caustic scrubber 358 serve another purpose. In particular, when used together these technologies effectively remove and/or destroy any biological elements that may be in the gas stream, by subjecting these elements extreme conditions, namely: adsorption, filtration to sub-micron levels, high temperatures, and caustic environments.

With further reference to FIG. 3, the gas is again passed though a gas cooler 362 and moisture separator 364. An optional gas chiller 368 is then used to reduce the gas dewpoint, thus further separating excess water and particulates. This condensate is removed by another moisture separator 372. The product gas is then compressed with a gas compressor 374 to increase the pressure of the gas. By way of example, the gas compressor 374 may comprise a positive displacement, flooded screw, sliding vane, or any other type of gas compressor for compressing the gas to the desired level. One embodiment features a lubrication-free compressor system to avoid reintroducing contaminants to the process gas. The temperature of the gas is once again lowered and condensate removed using a gas cooler 378 and moisture separator 382. The gas is then passed though a temperature swing adsorption system 384, which may comprise one or more vessels with a solid molecular sieve or desiccant type media such as activated carbon, silica gel, zeolite, and/or alumina. A gas heater may be used to heat a slip stream of gas to regenerate the offline bed. Beds may be alternated through a valve sequence to alternate gas flow through the active and regenerating bed(s). A final gas polishing vessel 388 filled with media is used to further clean the gas. Media may include without limitation: activated carbon, silica gel, zeolite, and/or alumina. In one embodiment, the resulting product gas 392 is approximately 100° F. and approximately 350 PSIG.

Figure 4:
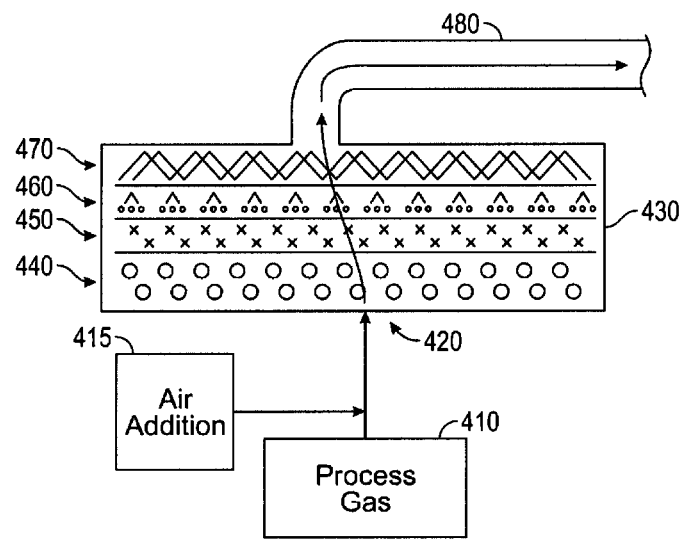
FIG. 4 is a diagram illustrating the use of a biological $H_2S$ removal system in accordance with an embodiment of the invention.

FIG. 4 is a diagram illustrating the use of a biological $H_2S$ removal system 400 in accordance with an embodiment of the invention. In particular, a system such as a pressure swing adsorption (PSA) system or a water scrubbing system may be employed to separate $H_2S$ into a process gas stream 410. Other systems may be employed for separating the $H_2S$ including without limitation: membrane systems, cryogenic systems, solvent-based systems, etc. However, in embodiments featuring a PSA system for removing $H_2S$ into a process gas stream 410, no oxygen is present in the gas stream 410. As such, the biological $H_2S$ removal system 400 includes air addition 415 (e.g., via blower or compressor) that allows for the proper metering of air 415 into the process gas stream 410 to achieve the correct concentration for biological use before release into the atmosphere or destruction. Alternatively, a different source of oxygen may be employed in lieu or in addition to the air addition. Similarly, the process gas stream from a water scrubbing system may include no oxygen, or less than the needed 2% oxygen. In such cases, the air addition 415 (e.g., via blower or compressor) is employed to enable the proper metering of air 415 into the gas stream 410 to achieve the correct concentration for biological use before release into the atmosphere or destruction.

In particular, process gas stream 410 (e.g., from an anaerobic digestion system 100 or a landfill gas system 200) is fed into a gas inlet 420 of the $H_2S$ removal system 400, which comprises a housing 430 including a plurality of layers 440, 450, 460, 470 through which the process gas stream flows. The treated gas exits the housing through a gas outlet 480, which feeds the gas stream into an anaerobic digester cleanup system or a landfill gas cleanup system. The gas inlet 420 may comprise one or more apertures disposed in the bottom of housing 430. Alternatively, the gas inlet 420 may be part of a gas inlet manifold that evenly distributes the gas within the housing 430. In the illustrated embodiment, the first (lower) layer 440 comprises a first mixing media, the second layer 450 comprises a second mixing media, the third layer 460 comprises a sprayer of a solution for $H_2S$ removal, and the fourth (upper) layer 470 comprises activated carbon.

With continued reference to FIG. 4, the first and second mixing media layers 440, 450 may comprise any suitable corrosion resistant materials including, but not limited to, plastic, ceramic, metal, mixing balls, raschig rings, and foam. These mixing media layers 440, 450 form various contoured shapes to facilitate mixing. In some embodiments, the first mixing media layer 440 is the same as the second mixing media layer 450. In other embodiments, these layers 440, 450 are different materials. The third layer sprayer 460 may be used to spray a suitable wash solution or neutralizing agent on the gas as it flows through the biological $H_2S$ removal system 400. Suitable agents comprise water solutions (with or without nutrients), caustic solutions, and basic solutions such as NaOH solutions of varying pH. The activated carbon layer 470 is employed to remove $H_2S$ from the process gas stream. As illustrated, the gas outlet 480 may comprise an outlet manifold having one or more openings distributed across the top of the housing 430 for achieving a substantially regular flow rate of gas within the housing 430.

According to further embodiments of the invention, other process streams with $H_2S$ and no oxygen can be handled similarly. Such gas streams may be byproducts of certain biological laboratory and factory processes. It is proposed that a biological $H_2S$ removal system in accordance with the above-described embodiments be used in these and similar applications.

Another embodiment of the invention is directed toward a method for the treatment of process gas for biological $H_2S$ removal, comprising: receiving a process gas stream from an anaerobic digestion system or from a landfill gas system; adding air to the process gas stream; passing the process gas stream through a gas inlet of a housing; treating the process gas stream for $H_2S$ removal; and passing a treated gas stream through a gas outlet in the housing.

The above method may further comprise the step of using a pressure swing adsorption system or a water scrubbing system to separate the $H_2S$ into a sour gas stream from another prior to adding air to the sour gas stream. Additionally, adding air to the sour gas stream may comprise metering the air into the process gas stream to achieve a predetermined oxygen concentration for biological use before release into the atmosphere or destruction. In some embodiments, the method may further comprise the step of feeding the treated gas stream into an anaerobic digester cleanup system or a landfill gas cleanup system. Treating the sour gas stream for $H_2S$ removal may comprise spraying the process gas stream with a neutralizing agent such as water solutions (with or without nutrients), caustic solutions, and basic solutions such as NaOH solutions of varying pH for $H_2S$ removal.

Figure 5:
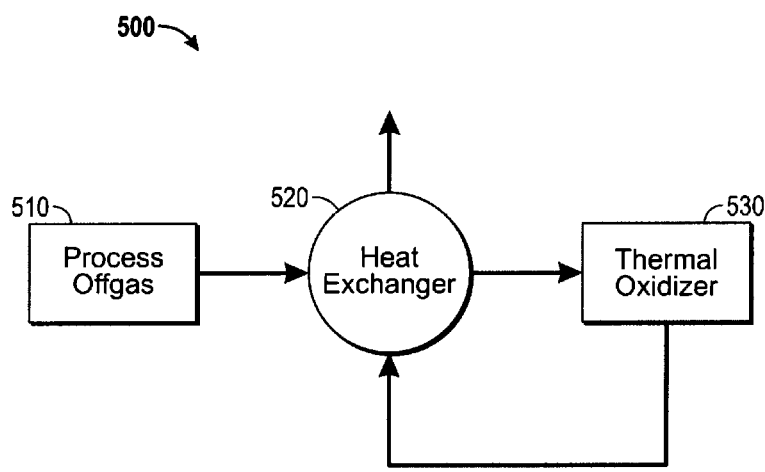
FIG. 5 is a diagram illustrating the use of a regenerative thermal oxidizer system 300 in accordance with an embodiment of the invention.

FIG. 5 is a diagram illustrating the use of a regenerative thermal oxidizer system 300 in accordance with an embodiment of the invention. The regenerative thermal oxidizer system 300 is configured to be used as part of an anaerobic digestion system 100 such as disclosed with respect to FIG. 1 and a landfill gas system 200 such as disclosed with respect to FIG. 2. In particular, process exhaust gas 310 from the anaerobic digestion system 100 or landfill gas system 200 is fed into a recuperative heat exchanger 320, which boosts the inlet temperature and feeds the gas into a regenerative thermal oxidizer 330. This process exhaust gas 310 is excess gas, e.g., from an anaerobic digestion system 100 or a landfill gas system 200, that would normally be destroyed using a flare or standard non-regenerative thermal oxidizer.

With further reference to FIG. 5, the thermal oxidizer 530 heats the gas such that it exits the thermal oxidizer at a much higher temperature and is fed back through the recuperative heat exchanger 520, which recoups the excess heat and lowers the temperature of the gas. By way of example, the process exhaust gas 510 may be fed into the heat exchanger 520 at a temperature of about 90° F. and is boosted to about 400° F. before entering the regenerative thermal oxidizer 530. In this example, the regenerative thermal oxidizer 530 may raise the gas temperature to about 1200° F. and the heat exchanger then reduces the temperature to about 500° F. By boosting the gas temperature, the recuperative heat exchanger 520 allows the thermal oxidizer 530 to operate without the use of additional fuel.

It is desirable that plant processes such as anaerobic digestion systems 100 and landfill gas systems 200 operate at the highest efficiency possible. In such processes, this requires very low levels of methane loss in the exhaust/off gas. However, while a low methane exhaust gas stream is great for plant efficiency, it is not good for a flare or the thermal oxidizer. In particular, if the plant is too efficient, a typical thermal oxidizer system may require the addition of supplemental fuel to maintain stable combustion, thereby reducing the overall plant efficiency.

A typical thermal oxidizer requires approximately 10-30% $CH_4$ to maintain stable combustion. By contrast, the regenerative thermal oxidizer 530 in the embodiment of FIG. 5 can operate with as low as 0.5% $CH_4$, thus allowing for a substantial increase in plant processing efficiency. This is achieved by allowing the incoming reactants to be reheated with the effluent hot gas from the thermal oxidizer exhaust gas stream. Accordingly, the regenerative thermal oxidizer 530 significantly increases plant efficiency by eliminating the penalty associated with conventional thermal oxidizers.

A further embodiment of the invention is directed toward a method for using a regenerative thermal oxidizer, comprising: receiving at a recuperative heat exchanger process exhaust gas from an anaerobic digestion system or a landfill gas system; boosting an inlet temperature of the gas to a second exhaust temperature; receiving at a regenerative thermal oxidizer the gas from the heat exchanger; further heating/combusting the gas to a third exhaust temperature; feeding the gas back through the recuperative heat exchanger; and recouping heat from the gas such that the gas exits the heat exchanger at a fourth gas temperature.

According to some embodiments of the above method, the inlet temperature of the exhaust gas is about 90° F., the second gas temperature is about 400° F., the third gas temperature is about 1200° F., and the fourth gas temperature is about 500° F. Boosting the inlet temperature of the gas to the second gas temperature may comprise allowing the thermal oxidizer to operate without the use of additional fuel or minimal fuel.

Figure 6:
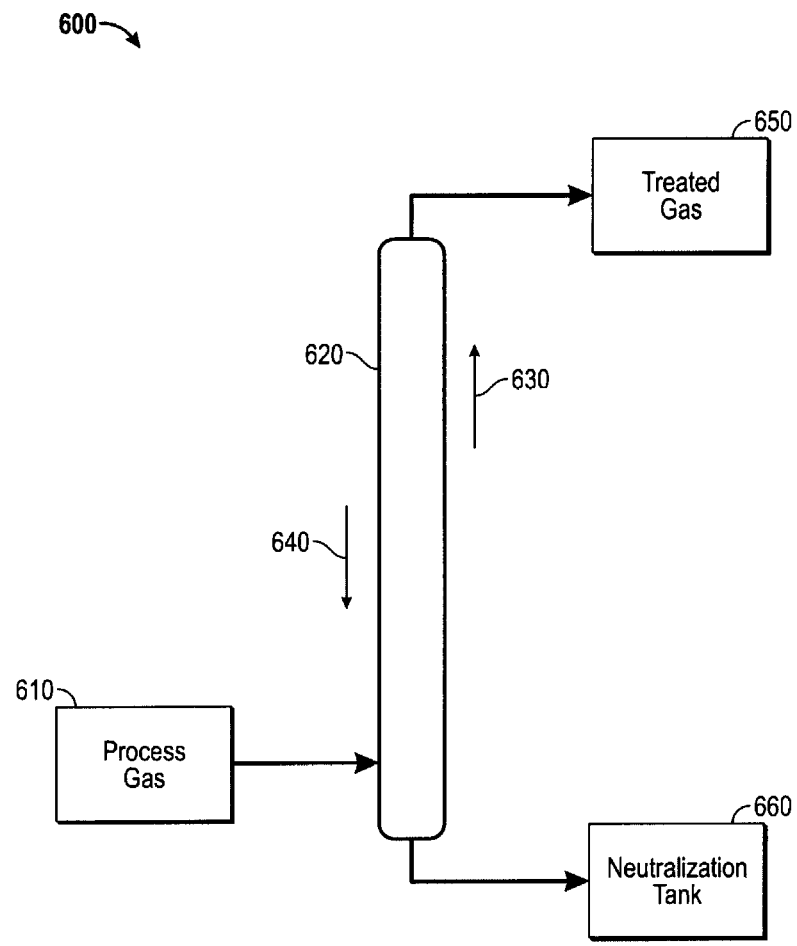
FIG. 6 illustrates the use of a caustic scrubber system in accordance with an embodiment of the invention.

FIG. 6 is a diagram illustrating the use of a caustic scrubber system 600 in accordance with an embodiment of the invention. In particular, process gas 610 (e.g., from an anaerobic digestion system 100 or a landfill gas system 200) is fed into the caustic scrubber 620. Process gas 610 contains at least one acid selected from the group consisting of $H_2S$, HF, $H_2SO_4$, $H_3PO_4$ and $HNO_3$. Such acids may be present in liquid and/or gaseous phases. According to various embodiments, the caustic scrubber 620 comprises a vertical column and includes a counter current flow system, wherein the gas stream travels up vertically through the column (as indicated by arrow 630) in counter current flow to a gravity trickling or sprayed caustic liquid solution that flows downward within the column (as indicated by arrow 640). The caustic liquid solution comprises a basic solution that is employed to neutralize various acids that are likely to be present in the process gas 610 such as $H_2S$, HF, $H_2SO_4$, $H_3PO_4$ and $HNO_3$. By way of example, the caustic liquid solution may comprise an NaOH solution. This process results in treated gas 650 that is substantially free of acids bubbling out through an opening at the top of the caustic scrubber 620. The spent caustic liquid solution containing acids flows through an opening in the bottom of the column and into a neutralization tank 660.

With further reference to FIG. 6, the treated gas 650 that is substantially free of acids flows back into the anaerobic digestion system 100 (FIG. 1) or the landfill gas system 200 (FIG. 2). In order to protect downstream metallurgy and equipment, a caustic scrubber 620 may be located, for example, between the anaerobic digester 130 and the biogas handling system 140 (FIG. 1) in order to protect the biogas handling system 140 and other downstream equipment from corrosion and other deleterious effects. Additionally, a caustic scrubber 620 may be located between the landfill gas wells 220 and the landfill gas processing and treatment plant 240 (FIG. 2) or within the plant (FIG. 3) in order to protect the landfill gas processing and treatment plant 240 and other downstream equipment from corrosion. According to some embodiments of the invention, the caustic scrubber allows for the total removal of acids such as $H_2S$, HF, $H_2SO_4$, $H_3PO_4$ and $HNO_3$ from the gas stream so that acid concentration cannot occur in any downstream areas regardless of changing dew point and condensation.

Another embodiment of the invention comprises a method of using a caustic scrubber for the treatment of process gas from an anaerobic digestion system. In particular, the method may entail: (i) receiving a process gas stream from the anaerobic digestion system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids an opening at the top of the vertical column; and (v) flowing the treated gas into an anaerobic digestion cleanup system.

A further embodiment of the invention comprises a method of using a caustic scrubber for the treatment of process gas from a landfill gas system. Specifically, the method may entail: (i) receiving a process gas stream from the landfill gas system; (ii) flowing the process gas stream up vertically through a vertical column; (iii) flowing a caustic liquid solution downward through the vertical column such that the caustic liquid solution removes at least one acid from the process gas stream; (iv) bubbling out treated gas that is substantially free of acids an opening at the top of the vertical column; and (v) flowing the treated gas into a landfill gas cleanup system.

One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The invention claimed is:

1. A system for the purification of biogas, comprising:
   a gas compressor for increasing the pressure of the biogas for processing;
   a gas processor for removing any $CO_2$, volatile organic compounds, and $H_2S$, from the gas;
   a biological sulfur removal system for treating offgas from the gas processor;
   a regenerative thermal oxidizer system for treating gas from the biological sulfur removal system for thermal destruction of volatile organic compounds, $H_2S$, and $CH_4$ slipped from the gas processor;
   a catalytic oxygen removal system for receiving product gas from the gas processor and removing oxygen from the product gas; and
   a caustic scrubber for receiving product gas from the catalytic oxygen removal system and neutralizing any acid formed during catalytic oxygen removal.

2. The system of claim 1, wherein the biological sulfur removal system comprises a housing that receives gas from the gas processor through a gas inlet, and wherein the housing comprises a plurality of layers through which the gas flows while it is treated for $H_2S$ removal, and a gas outlet through which treated gas exits.

3. The system of claim 2, wherein a first layer comprises a lower layer including a first mixing media, and wherein a second layer is disposed above the first layer and comprises a second mixing media.

4. The system of claim 3, wherein a third layer is disposed above the second layer and comprises at least one sprayer of a solution for $H_2S$ removal.

5. The system of claim 4, wherein the at least one sprayer is used to spray a solution on the gas as it flows through the housing.

6. The system of claim 5, wherein the solution is selected from the group consisting of: water solutions, caustic solutions, and basic solutions such as NaOH solutions of varying pH for $H_2S$ removal.

7. The system of claim 4, wherein a fourth layer comprises a top layer of activated carbon disposed above the third layer.

8. The system of claim 1, wherein the regenerative thermal oxidizer system comprises:
   a recuperative heat exchanger that receives gas from the biological sulfur removal system or gas processor and boosts an inlet gas temperature of the gas to a second gas temperature; and
   a regenerative thermal oxidizer that receives the gas from the heat exchanger, further heats the gas to a third exhaust temperature, and feeds the gas back through the recuperative heat exchanger, which recoups heat from the gas such that the exhaust exits the heat exchanger at a fourth gas temperature.

9. The system of claim 1, wherein the caustic scrubber comprises a vertical column having a top and a bottom and including a counter current flow system, wherein the process gas flows up vertically through the column in counter current flow to a caustic liquid solution that flows downward through the column.

10. The system of claim 9, wherein the caustic liquid solution removes at least one acid from the process gas such that treated gas that is substantially free of acids bubbles out through an opening at the top of the vertical column.

11. The system of claim 10, wherein the at least one acid is selected from the group consisting of $H_2S$, $HF$, $H_2SO_4$, $H_3PO_4$ and $HNO_3$.

12. The system of claim 9, wherein the caustic liquid solution comprises an NaOH solution.

* * * * *